(12) United States Patent
Woydziak

(10) Patent No.: US 12,329,747 B2
(45) Date of Patent: Jun. 17, 2025

(54) USE OF LIPOPHILIC BETA-LACTAM ANTIBIOTICS AND CARBOXYLATE ESTERS FOR THE TREATMENT OF BACTERIAL INFECTIONS WITHIN CITRUS AND OTHER PLANT SPECIES

(71) Applicant: BOARD OF REGENTS OF THE NEVADA SYSTEM OF HIGHER EDUCATION ON BEHALF OF NEVADA STATE COLLEGE, Henderson, NV (US)

(72) Inventor: Zachary R. Woydziak, Henderson, NV (US)

(73) Assignee: Board of Regents of the Nevada System of Higher Education on behalf of Nevada State College, Henderson, NV (US)

( * ) Notice: Subject to any disclaimer, the term of this patent is extended or adjusted under 35 U.S.C. 154(b) by 329 days.

(21) Appl. No.: 16/746,050

(22) Filed: Jan. 17, 2020

(65) Prior Publication Data
US 2020/0230114 A1    Jul. 23, 2020

Related U.S. Application Data

(60) Provisional application No. 62/795,165, filed on Jan. 22, 2019.

(51) Int. Cl.
A61K 31/43      (2006.01)
A01N 43/90     (2006.01)
A61K 31/431    (2006.01)

(52) U.S. Cl.
CPC .............. *A61K 31/43* (2013.01); *A01N 43/90* (2013.01); *A61K 31/431* (2013.01)

(58) Field of Classification Search
CPC ...... A61K 31/43; A61K 31/431; A61K 47/46; A01N 43/90
See application file for complete search history.

(56) References Cited

U.S. PATENT DOCUMENTS 3,832,347 A    8/1974    Lammert et al.
3,880,872 A    4/1975    Kukolja et al.
5,637,579 A    6/1997    Hubschwerlen et al.

OTHER PUBLICATIONS

Zhang et al, PLOS One 2014, vol. 9(11), pp. 1-11. (Year: 2014).*
Zhang et al, Phytopathology 2010, vol. 100, pp. 239-245. (Year: 2010).*

(Continued)

*Primary Examiner* — Marianne C Seidel
*Assistant Examiner* — Janet L Coppins
(74) *Attorney, Agent, or Firm* — Reising Ethington P.C.

(57) ABSTRACT

Disclosed is method for converting a beta-lactam antibiotic into a "masked" beta-lactam antibiotic to permit it to cross the waxy cuticle of a plant and then subsequently unmasking the beta-lactam and converting it into an active beta-lactam antibiotic in the plant phloem. The method permits the use of beta-lactam antibiotics to be used to treat a variety of plant bacterial infections that was not previously possible because the native beta-lactam antibiotics cannot cross the waxy cuticle of plants. In one embodiment the disclosure finds special use in the treatment of bacterial infection of citrus plants with Huanglongbing disease.

13 Claims, 16 Drawing Sheets

(56) References Cited

OTHER PUBLICATIONS

Figure 1:
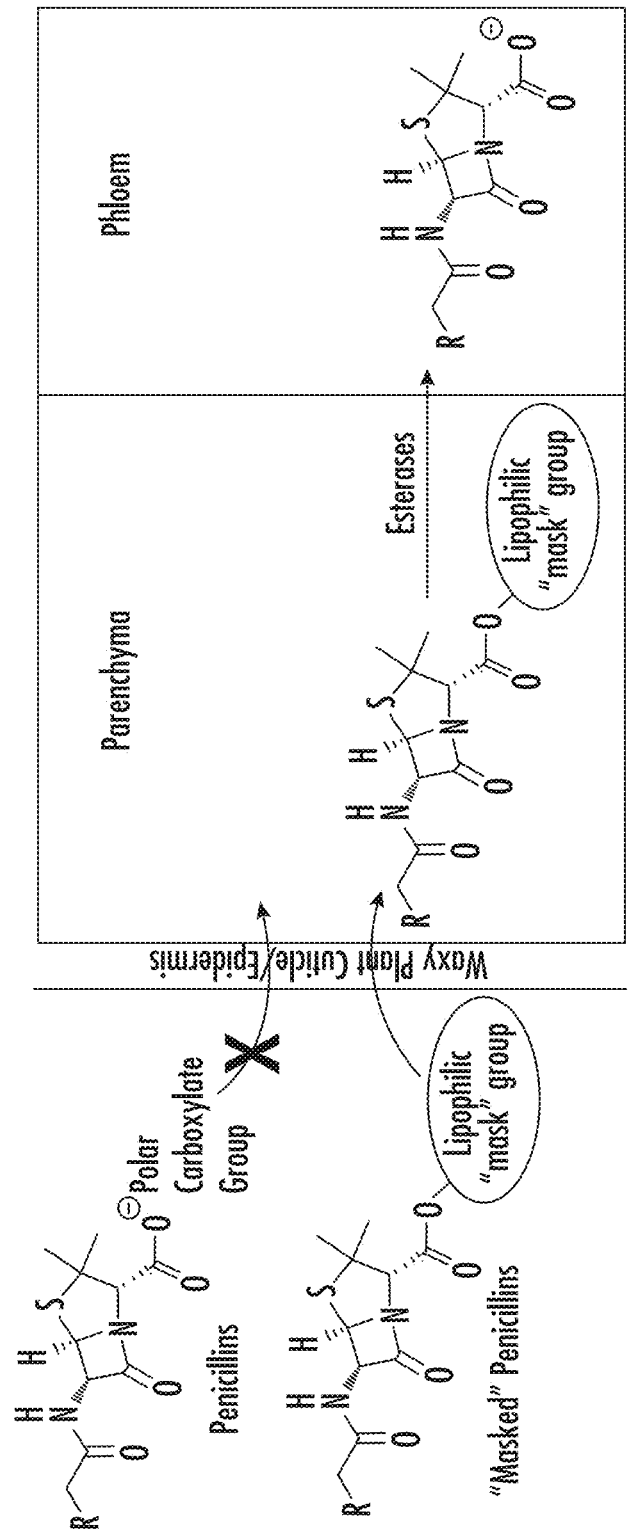
Figure 2A:
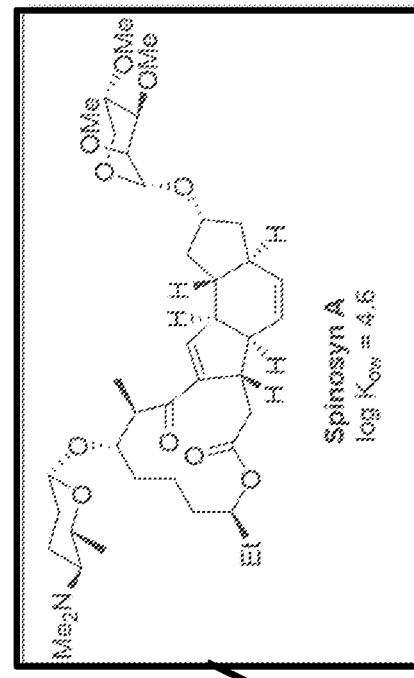
Figure 2B:
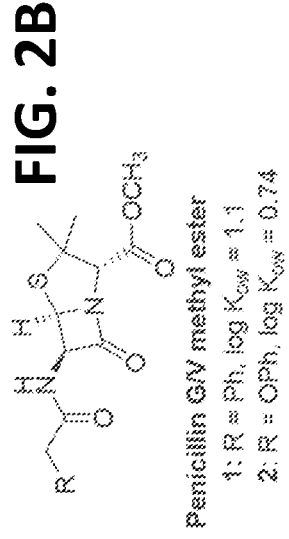
Figure 2C:
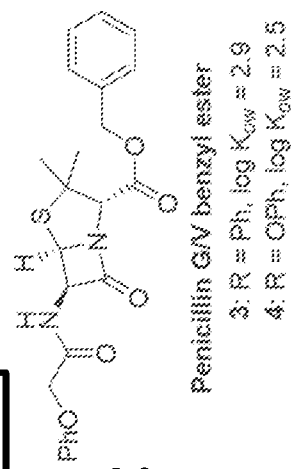
Figure 2D:
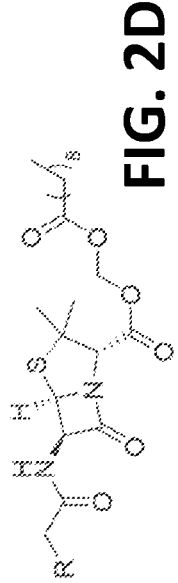
Figure 2E:
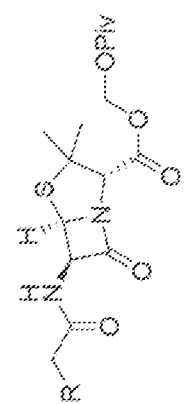
Figure 2F:
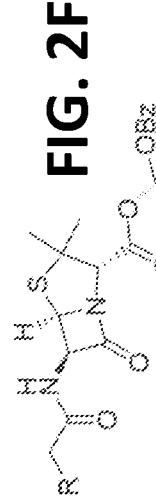

Laws et al, J Chem Soc Perkin Trans. II 1989, pp. 1577-1581 (Year: 1989).*
PubChem record of Penicilin G, web printout of https://pubchem.ncbi.nlm.nih.gov/compound/5904, 2004, pp. 1-50 (Year: 2004).*
Web printout of https://gardinwarehouse.com/blogs/garden-science/foliar-spray-how-does-a-plant-absorb-nutrients-through-its-leaves, published Jan. 19, 2018, pp. 1-4, accessed Sep. 10, 2022. (Year: 2018).*
Zhang et al., Adv Antibiotics Antibodies 2015, 1:1, pp. 1-2. (Year: 2015).*
Yang et al., PLOS ONE 2015, 10(7), 1-14. (Year: 2015).*
Lieberman et al., The Practice of Medicinal Chemistry 2015, Chapter 32, pp. 767-791. (Year: 2015).*
Yang et al., PLOS One (2015), 10(7), pp. 1-14. (Year: 2015).*
Andrew P. Laws and Michael I. Page, The Effect of the Carboxy Group on the Chemical and p-Lactamase Reactivity of p-Lactam Antibiotics, J. Chem. Soc.Perkin Trans. II Jan. 1989, XP055684497.
Indian 1st Examination Report, IN Application No. 202147032523, Applicant: Board of Regents of the Nevada System of Higher Education on Behalf of Nevada State College, Date: Sep. 15, 2021.
MX Office Action for MX Application No. MX/a/2021/008682 dated Jan. 16, 2025, (6 pages).
BR Office Action for BR Application No. 112021014369.6 dated Feb. 4, 2025, (4 pages).

* cited by examiner

USE OF LIPOPHILIC BETA-LACTAM ANTIBIOTICS AND CARBOXYLATE ESTERS FOR THE TREATMENT OF BACTERIAL INFECTIONS WITHIN CITRUS AND OTHER PLANT SPECIES

RELATED APPLICATIONS

This application claims priority to U.S. Provisional Patent Application No. 62/795,165, filed Jan. 22, 2019, which is incorporated herein by reference in its entirety.

STATEMENT REGARDING FEDERALLY SPONSORED RESEARCH

NONE.

TECHNICAL FIELD

This disclosure relates generally to horticulture and more particularly to methods and materials for treatment of bacterial infections of plants.

BACKGROUND OF THE INVENTION

This section provides background information which is not necessarily prior art to the inventive concepts associated with the present disclosure. Plants and in particular commercially important plants are subject to a variety of bacterial infections. Many times these bacterial infections are a secondary result of the plants being attacked by any of a variety of insects. Plant growers have treated plants with a variety of insecticides and other treatment regimes in an attempt to rid the plants of the insect vectors or to overcome the bacterial infections or to at least control them.

The plant disease Huanglongbing (HLB), which is more commonly known as "citrus greening", is a bacterial infection which damages the phloem of all plants in the genus of *Citrus*. This disease has been attributed to three species of α-proteobacteria in the genus *Candidatus* Liberibacter; specifically, *Candidatus* Liberibacter asiaticus, *Candidatus* Liberibacter africanus and *Candidatus* Liberibacter americanus. The disease has been known throughout the world for over a century. The disease has devastated the citrus industry in Florida over the course of the last decade, and is just beginning to spread into California and Texas. Currently over 80% of the commercial citrus plant industry in Florida is infected with the subject bacteria. It has also spread outside the United States to numerous countries in Asia, Africa, the Indian subcontinent, the Arabian Peninsula, and South and North America. The countries of Mexico, China, India and Brazil, among the top five citrus producing countries in the world's agricultural output, have also been heavily impacted by this disease. Currently, no commercial treatments for the disease are available to completely rid the plant of the harmful bacteria and it is 100% fatal to an infected plant. Once a plant contracts the disease, it will inevitably become unproductive over several seasons, due to an inability to transfer nutrients and sugar, and eventually it will die. Extensive attempts have been made to treat the vector carrier insects of the bacteria; the Asian citrus psyllid (ACP, *Diaphorina citri* Kuwayama) and the *Trioza erytreae*, using traditional pesticides, but these attempts at best have only slowed the rate of transmission from one plant to another. The bacterium is injected directly into the vascular system, phloem, of the citrus tree by the vector and can spread systemically throughout the tree. There are currently no HLB resistant cultivars available.

The most common methods for treating bacterial plant infections are treatment with oxytetracycline hydrochloride, treatment with streptomycin sulfate or treatment with copper. Copper has not been found to be effective against HLB and thus it is not used. The citrus industry is currently spraying HLB infected trees with oxytetracycline hydrochloride and streptomycin sulfate antibiotics, these drugs are most commonly used to prevent fire blight (*Erwinia amylovera*) in apples and pears. Streptomycin is preferred for use against fire blight since it is bactericidal while the oxytetracyline is only bacteriostatic. Neither one of these treatments have been shown to do more than only marginally improved the health of trees infected with HLB. While cheaper and more historical beta-lactam type antibiotics such as penicillin G and penicillin V are extremely effective against the pathogenic bacteria in laboratory testing using a grafting method and express very little phytotoxicity, these highly polar antibiotics do not easily penetrate the waxy cuticle covering of the epidermis layer of citrus leaves or stems to gain access to the phloem where the bacteria reside. Thus, external application of penicillin and other beta-lactams to the plant are not an effective means for treating diseased plants. A number of studies have shown that Penicillin G alone or in combinations with other antibiotics, when direct injected into infected citrus trees, shows a marked improvement in the tree's health. However, injecting large numbers of trees in an infected commercial orchard would be highly impractical, very costly and no penicillins are currently registered for use in plants.

It is desirable to provide an antibacterial treatment for HLB that is highly effective and able to enter the phloem, that utilizes a low level of antibacterial agent and that can be easily applied to large numbers of plants in an efficient manner.

SUMMARY OF THE DISCLOSURE

This section provides a general summary of the disclosure and is not a comprehensive disclosure of its full scope or all features, aspects or objectives.

The present disclosure provides a method for esteric modification of a carboxylate functionality in a beta-lactam antibiotic which allows the ester modified beta-lactam antibiotic to rapidly penetrate the waxy cuticle layer on the epidermis of plant leaves or stems, in particular citrus plants, to access the phloem. During the movement from the cuticle layer to the phloem the ester functionality is converted back to the carboxylic function either through the action of cellular esterases or via acid hydrolysis. The converted compound is the active beta-lactam antibiotic. The modified beta-lactam can be efficiently applied to a large number of plants by foliar application and is readily and rapidly taken up into the phloem of the plant, during this movement it is converted back to the active antibiotic agent through the action of cellular esterases or via hydrolysis. The present disclosure and method can be used to modify a variety of beta-lactam antibiotics to make them applicable for use in a variety of plants. The method includes the conversion of the carboxylic function of the beta-lactam into an ester, which permits the beta-lactam to cross the waxy cuticle layer through the epidermis and to gain access to the phloem. During the movement through the plant layers the ester functionality is converted back to a carboxylate functionality. Once in the phloem the activated beta-lactam antibiotic is able to exert its beneficial effects.

In one embodiment the present disclosure is a method for treating a bacterial infection in a plant comprising the steps of: a) providing a beta-lactam antibiotic; b) converting a carboxylate functionality on the beta-lactam antibiotic to an ester function; and c) applying the ester functional beta-lactam from step b) to an outside surface of a plant having a bacterial infection in an amount sufficient to treat the bacterial infection.

These and other features and advantages of this disclosure will become more apparent to those skilled in the art from the detailed description of a preferred embodiment. The drawings that accompany the detailed description are described below.

BRIEF DESCRIPTION OF THE DRAWINGS

The drawings described herein are for illustrative purposes only of selected embodiments and not all implementations, and are not intended to limit the present disclosure to only that actually shown. With this in mind, various features and advantages of example embodiments of the present disclosure will become apparent from the written description when considered in combination with the appended Figures, wherein:

FIG. 1 is schematic description of one embodiment of the present disclosure;

FIG. 2A shows the structure of the PRIOR ART compound Spinosyn A, it is an insecticide that is known to penetrate citrus leaves, FIGS. 2B to 2F show the structures of a series of ester "masked" derivatives of Penicillin G and Penicillin V prepared according to the present disclosure, compounds 1 to 10 as described in the specification;

FIG. 3 is schematic of the $S_N2$ reaction process used according to the present disclosure to form the ester masked beta-lactam antibiotics shown in FIG. 2B;

FIG. 4 is the negative ESI Mass Spectrum for citrus clippings treated with product compound 1, FIG. 2B, according to the present disclosure;

FIG. 5 is the negative ESI Mass Spectrum for citrus clippings treated with product compound 2, FIG. 2B, according to the present disclosure;

FIG. 6 is the negative ESI Mass Spectrum for citrus clippings treated with product compound 3, FIG. 2C, according to the present disclosure;

FIG. 7 is the negative ESI Mass Spectrum for citrus clippings treated with product compound 4, FIG. 2C, according to the present disclosure;

FIG. 8 is the negative ESI Mass Spectrum for citrus clippings treated with product compound 5, FIG. 2D, according to the present disclosure;

FIG. 9 is the negative ESI Mass Spectrum for citrus clippings treated with product compound 6, FIG. 2D, according to the present disclosure;

FIG. 10 is the negative ESI Mass Spectrum for citrus clippings treated with product compound 7, FIG. 2E, according to the present disclosure;

FIG. 11 is the negative ESI Mass Spectrum for citrus clippings treated with product compound 8, FIG. 2E according to the present disclosure;

FIG. 12 is the negative ESI Mass Spectrum for citrus clippings treated with product compound 9, FIG. 2F, according to the present disclosure;

FIG. 13 is the negative ESI Mass Spectrum for citrus clippings treated with product compound 10, FIG. 2F, according to the present disclosure;

FIG. 14 is the negative ESI Mass Spectrum for citrus clippings treated with horticultural oil according to the present disclosure;

FIG. 15 is the negative ESI Mass Spectrum for citrus clippings treated with water according to the present disclosure; and FIG. 16 is a proposed scheme of the hydrolysis of product compounds 1 and 2 that is believed to occur in accordance with the present disclosure.

DETAILED DESCRIPTION OF A PREFERRED EMBODIMENT

The present disclosure is directed toward modification of beta-lactam antibiotics to enable them to cross the waxy cuticle layer and the epidermis of plants to gain access to the phloem. During this movement they are converted back to the active beta-lactam antibiotics and perform their antibiotic function. Water and minerals are absorbed by the roots of trees then transported throughout the tree by the xylem while the phloem transports organic materials synthesized in the leaves of the tree to other parts of the tree. As discussed above the bacterium believed to cause HLB is found in the phloem of infected trees. The bacterial infection interferes with transport of materials in the phloem and leads to death of the tree.

As discussed above, several of the beta-lactam antibiotics appear to be effective against HLB; however their polar nature, which is a function of the carboxylate group, prevents them from crossing the waxy cuticle layer and the epidermis to gain access to the bacteria in the phloem. The present disclosure is direct to a method for temporarily "masking" the carboxylate function using an ester modification and enabling the beta-lactam antibiotic to cross the waxy cuticle layer and epidermis of plants. FIG. 1 presents a schematic showing the concept of the present disclosure. As shown, a typical beta-lactam antibiotic is a penicillin and it includes a polar carboxylate functionality. This carboxylate functionality prevents it from crossing the waxy cuticle layer and epidermis of the plants. The present disclosure provides methods to "mask" the carboxylate function so that the "masked" penicillin can gain access to the phloem. In the present disclosure the masking groups are ester functional groups. In the present disclosure the carboxylate function of the beta-lactams is converted to an ester group to mask the polar carboxylate group. Although not bound to this theory, it is believed that the parenchyma cell esterases convert the ester "masked" beta-lactam back to the active carboxylate containing beta-lactam and restore antibiotic functionality.

In masking the carboxylate group, a number of relatively polar and water soluble penicillin derivatives such as penicillin G, penicillin V, methicillin, cloxacillin, dicloxacillin, flucloxacillin, nafcillin, oxacillin, mecillinam, and others can be converted to considerably more apolar and lipophilic forms. In Table 1 below the calculated log $K_{ow}$ values are shown for a series of beta-lactam antibiotics that have been converted to ester functions (B and C) versus the native carboxylate function (A). The log $K_{ow}$ values are the octanol/water partition coefficients for the compounds and represent the concentration in octanol/concentration in water for a compound in an octanol/water two partition solvent as known to one of skill in the art. The values show that converting to one of the two esters dramatically increases the log $K_{ow}$ values. The R group in the structures below varies by the actual beta-lactam as known to those of skill in the art. For example, for penicillin G the R group is a phenyl group.

TABLE 1

| 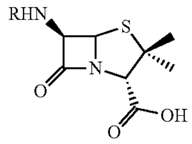  | 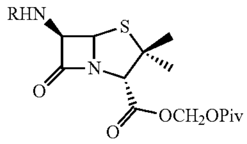  | 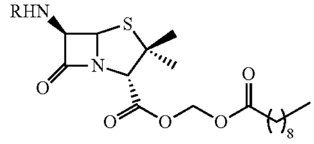  | |
|---|---|---|---|
| A | B | C | |
| Beta-lactam | Log $K_{ow}$ A[1] | Log $K_{ow}$ B[2] | Log $K_{ow}$ C[3] |
| Penicillin G | 1.75 | 3.02 | 5.08 |
| Penicillin V | 2.02 | 2.66 | 4.72 |
| Methicillin | 1.19 | 2.82 | 4.89 |
| Nafcillin | 2.10 | 4.28 | 6.35 |
| Oxacillin | 1.17 | 3.35 | 5.41 |
| Mecillinam | 1.17 | 3.35 | 5.41 |

1. The calculated $K_{ow}$ A values were calculated only based on the protonated beta-lactam, the carboxylate values would be even less. 2. The calculated values for the pivaloylmethoxy esters B. 3. The calculated values for the decanoylmethyloxy esters C.

Once these ester compounds are near the phloem, it is believed that the ester functionality is hydrolyzed, via esterase activity or acid catalyzed hydrolysis, back into the active antibiotic carboxylate functionality. The hydrolysis of the ester moiety allows the antibiotic to become both active and to regain its hydrophilic nature allowing the native antibiotic to be transported throughout the phloem network of the plant. The present inventor has developed a means by which he can deliver penicillin derivatives into the phloem of healthy citrus clippings through an external foliar application. These derivatives rely on a temporary lipophilic group which "masks" the highly polar carboxylate group in the penicillin core as shown in FIG. 1.

Figure 3:
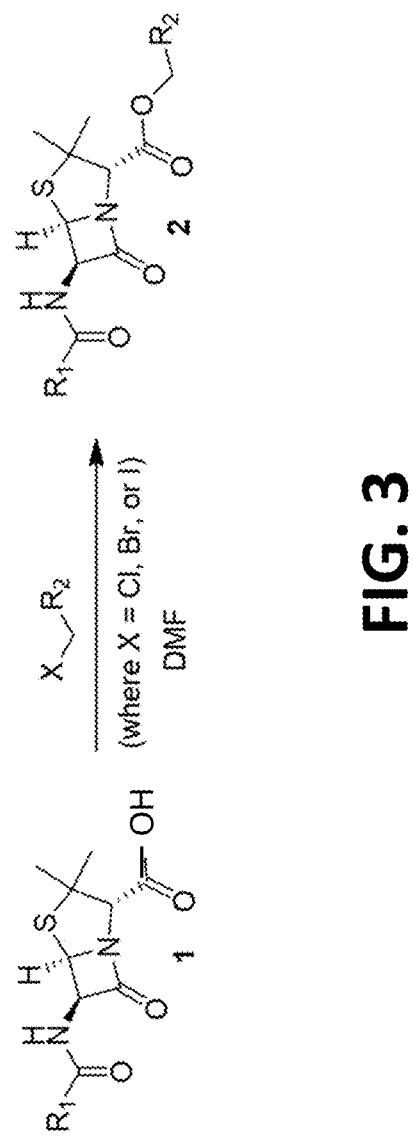
Figure 4:
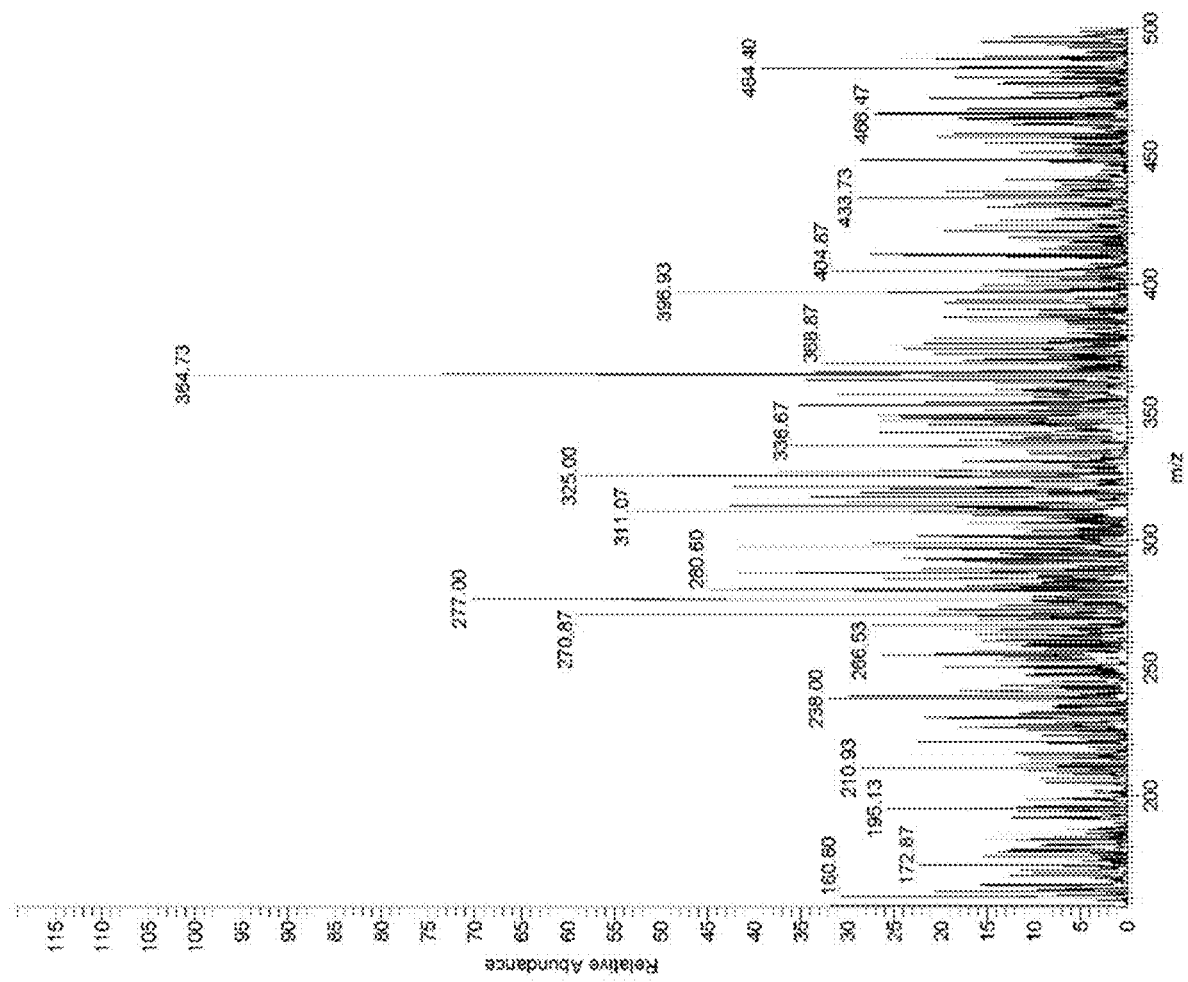
Figure 5:
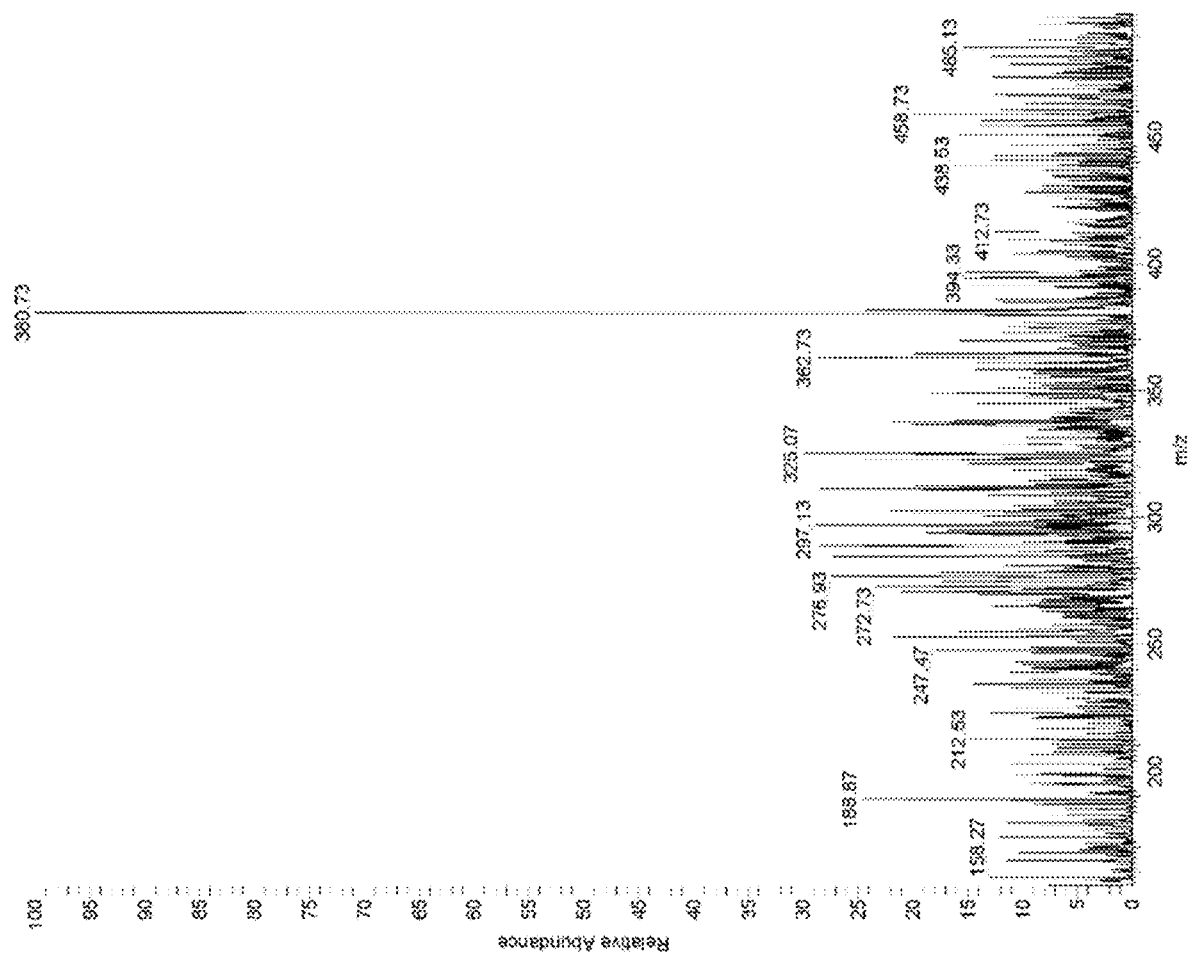
Figure 6:
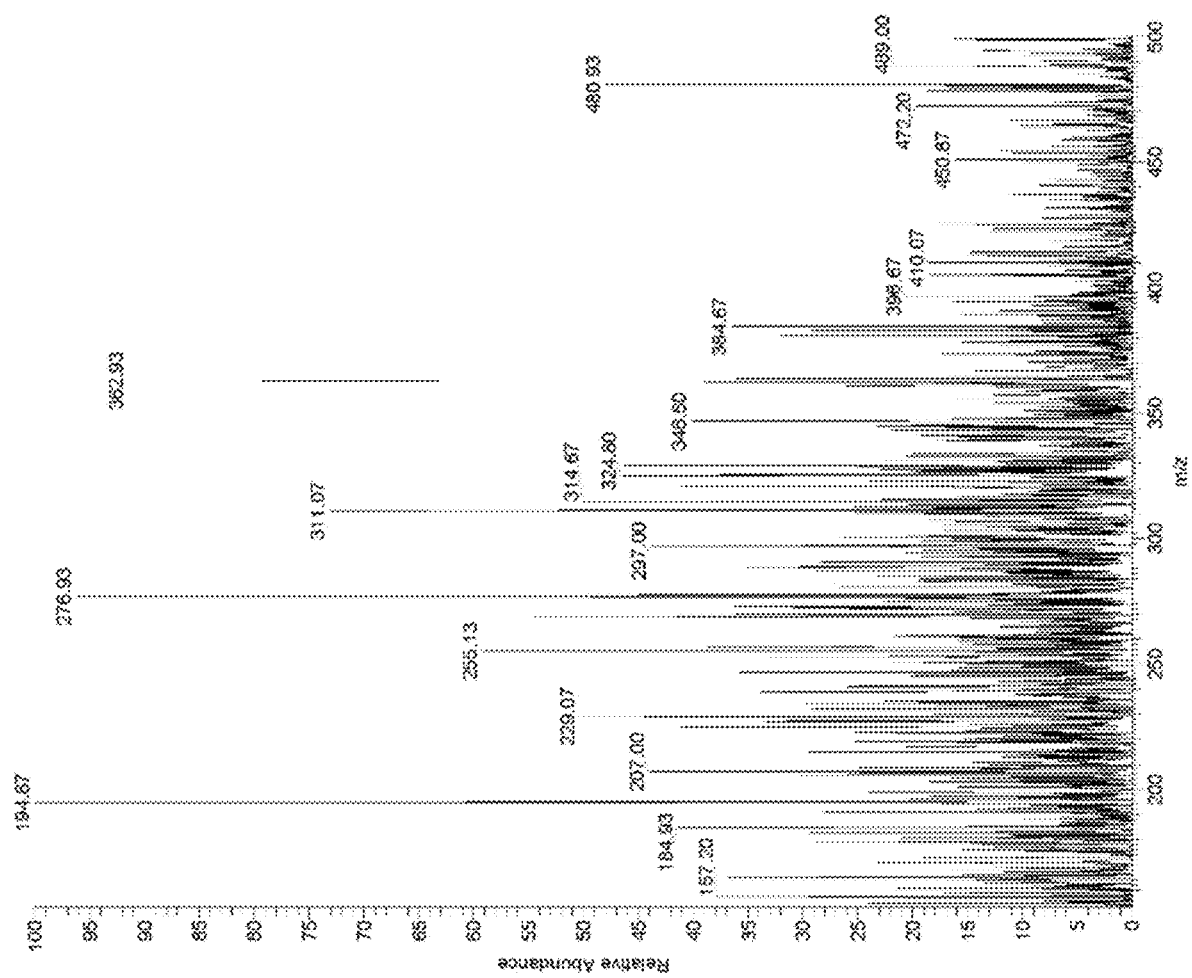
Figure 7:
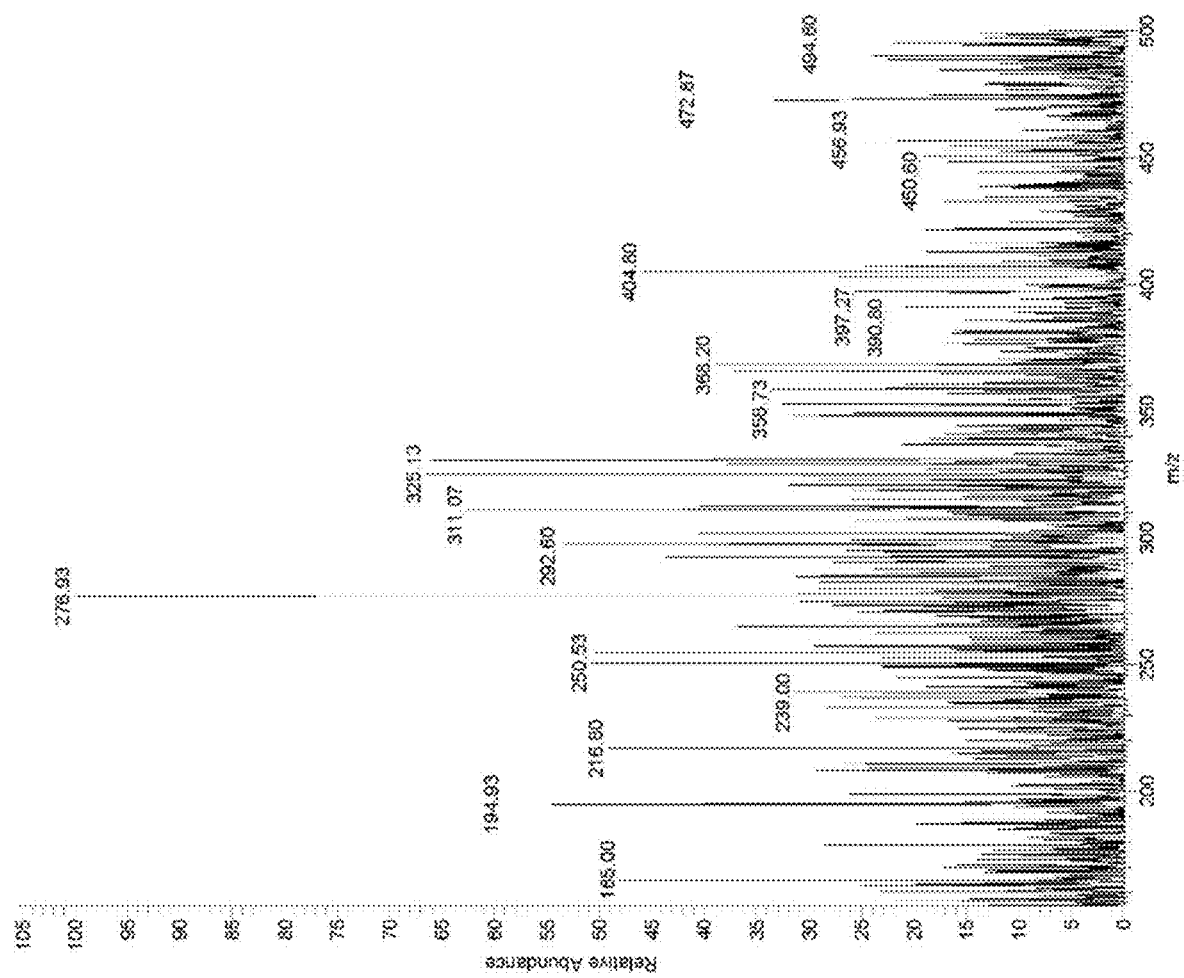
Figure 8:
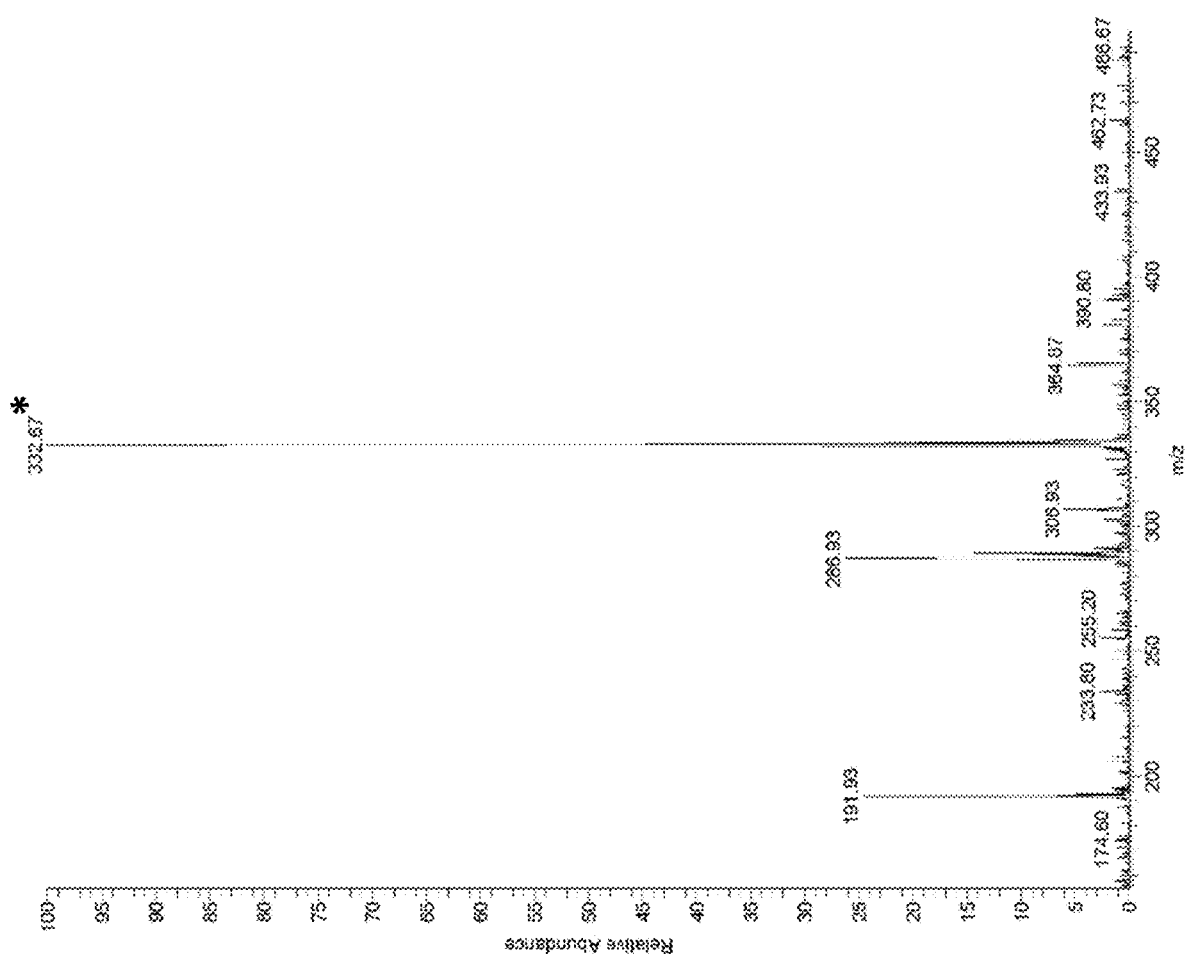
Figure 9:
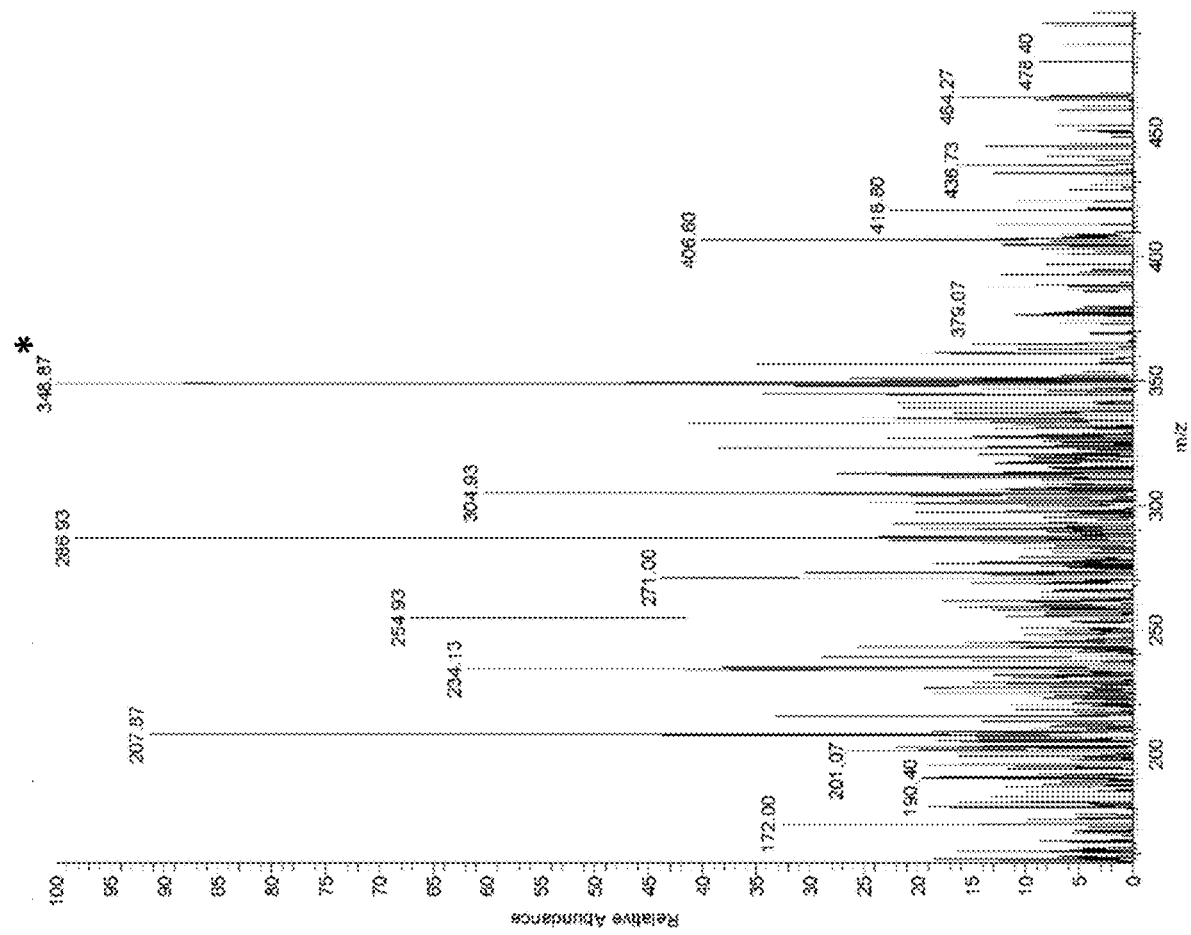
Figure 10:
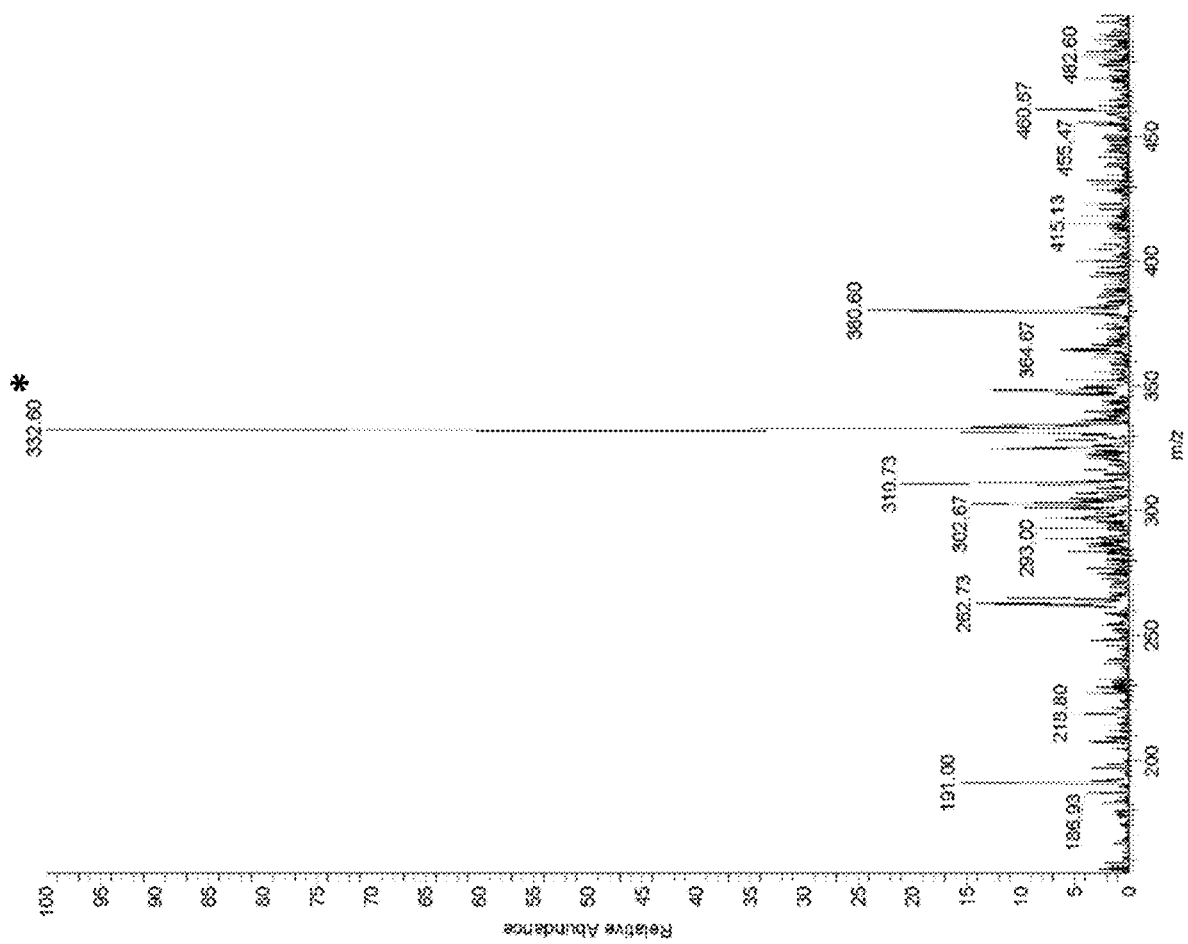
Figure 11:
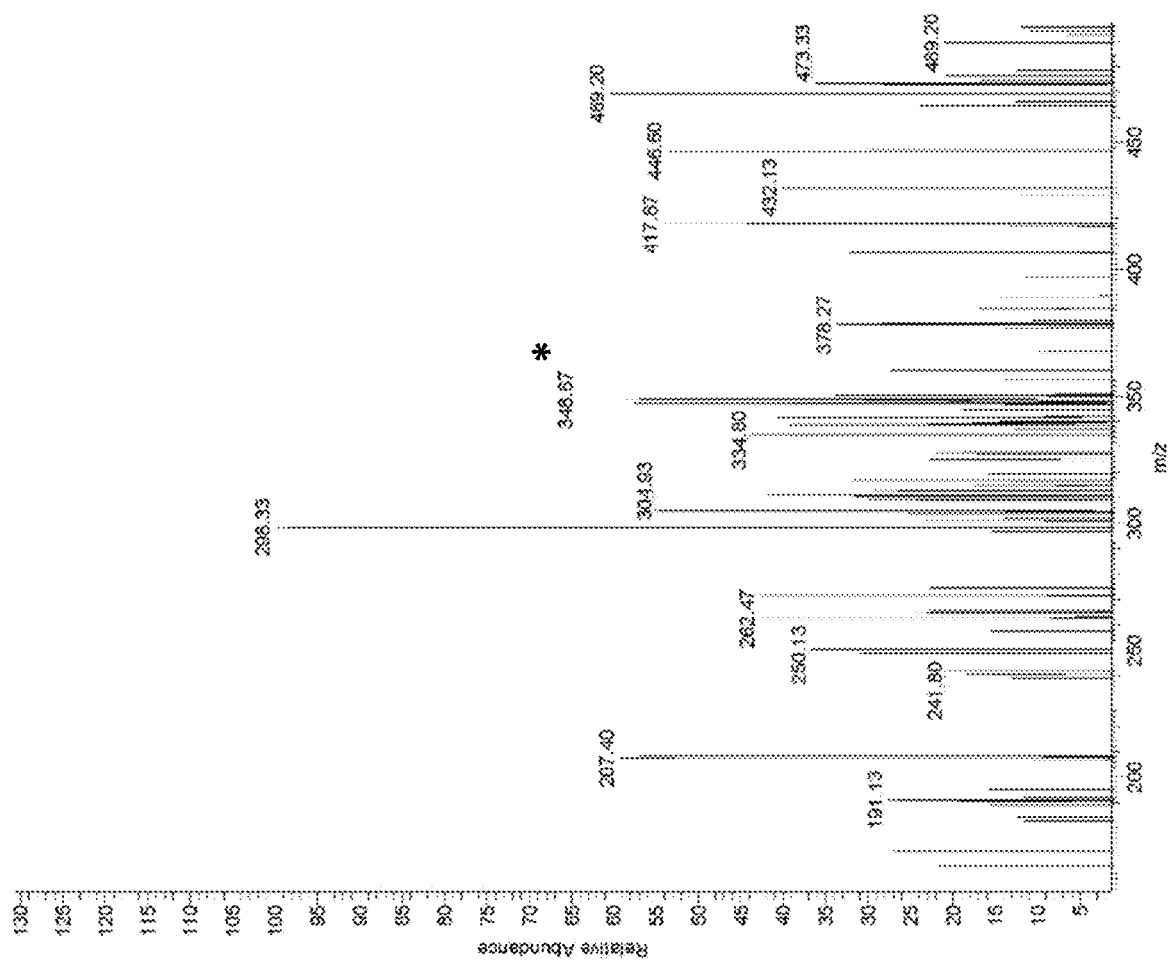

The present disclosure presents a method for "masking" beta-lactam antibiotics that comprises converting the carboxylate function into an ester function. This is accomplished by using the known nucleophilic substitution reaction mechanism, $S_N2$. A schematic of the reaction mechanism is shown in FIG. 3. In this particular scheme of the present disclosure the carboxylate attacks and displaces a halogen leaving group to install the ester group $R_2$; a method which is known in the literature for constructing penicillin esters. The preferred halogen leaving groups comprise chloride, bromide or iodide. The solvent can comprise any of a variety of standard organic solvents or water as is known in the art. Examples of these solvents include, by way of example and not limitation, N,N-dimethylformamide (DMF), dichloromethane, tetrahydrofyran (THF), acetonitrile and water.

EXPERIMENTAL PROCEDURES $^{1}H$ (400 MHz) and $^{13}C$ (101 MHz) NMR spectra were acquired on a Varian VNMRS-400 instrument using approximately 0.3 M solutions. Chemical shifts are reported in ppm (δ) and are referenced to $CDCl_3$, 7.27 ppm for $^{1}H$ and 77.0 ppm for $^{13}C$. Coupling constants Ali are in hertz and are reported as follows: chemical shift, multiplicity (br=broad, s=singlet, d=doublet, t=triplet, q=quartet, m=multiplet, hept=heptet, dt=doublet of triplets, dt=doublet of quartets, dd=doublet of doublets), coupling constant, and integration. Melting points were acquired using a Bibby scientific SMP10 melting point apparatus and are uncorrected. Infrared spectra (IR) were recorded with a Shimadzu GladiATR 10 Single Reflection ATR accessory. HPLC analysis was performed using a Beckman Coulter System Gold unit equipped with UV-Vis detection. High-resolution electrospray ionization (HR-ESI) mass spectra were obtained at the Mass Spectrometry Laboratory at the University of California, Irvine. Thin layer chromatography (TLC) used EMD aluminum-backed silica plates (0.20 mm, 60 F-254), and flash chromatography used ICN silica gel (200-400 mesh). Plates were visualized by UV or staining with ceric sulfate/molybdic acid. All commercial reagents and solvents were used as received unless otherwise noted. Yields are reported based on isolated material.

The general reaction process for forming the ester masked product compounds 1 to 10 shown in FIG. 2B to 2F was as follows. The beta-lactam, penicillin G, sodium salt, or penicillin V, potassium salt, 1.0 mmol, was combined with the solvent N,N-dimethylformamide, 10.0 mL, and the resulting mixture was stirred briefly before 10.0 mmol of an alkyl halide, an aryl halide or an oxymethyl alkyl or aryl halide was added. The resulting mixture was stirred for 1 hour at 26° C. and then the reaction was quenched by adding 20 mL of $H_2O$. The reaction time is preferably 5 hours or less, more preferably 2 hours or less, most preferably form 1 to 2 hours. Reaction times of longer than 5 hours lead to an increase in the side reaction products, which is undesirable. The aqueous mixture was extracted with 3×15 mL of diethyl ether and the combined organic fractions were dried over $Na_2SO_4$ and concentrated. The resulting residue was purified by flash column chromatography (15 g of ICN silica gel) using two sequential solvent systems: 10% ethyl acetate in hexanes (50 mL) followed by 10% methanol in $CH_2Cl_2$ (100 mL), to provide the corresponding beta-lactam ester product compound. Supporting spectral data for each of the synthesized ester compounds 1-10 in the library is provided below.

Compound 1

1

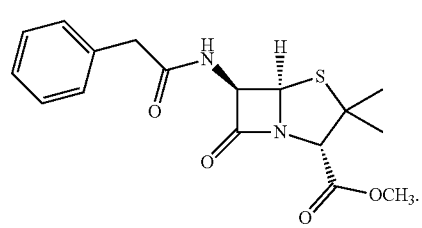

Methyl(2S,5R,6R)-3,3-dimethyl-7-oxo-6-(2-phenylacetamido)-4-thia-1-azabicyclo[3.2.0]heptane-2-carboxylate (1). A total of 320 mg (92%) methyl ester 1 was obtained as a colorless oil. $^1$H NMR (400 MHz, CDCl$_3$) δ 7.44-7.05 (m, 5H), 6.32 (d, J=8.9 Hz, 1H), 5.59 (dd, J=8.9, 4.2 Hz, 1H), 5.45 (d, J=4.2 Hz, 1H), 4.33 (s, 1H), 3.70 (s, 3H), 3.58 (s, 2H), 1.40 (s, 3H), 1.38 (s, 3H); $^{13}$C NMR (101 MHz, CDCl$_3$) δ 173.4, 170.5, 168.0, 133.9, 129.7, 128.8, 127.8, 127.3, 70.4, 68.0, 64.4, 58.9, 52.5, 43.2, 31.9, 26.9; IR (film) ν$_{max}$ 3364, 2963, 2924, 1782, 1744, 1690, 1499, 1451, 1180, 748, 694 cm$^{-1}$; HRMS (ESI) m/z 349.1209 (M+H$^+$, C$_{17}$H$_{21}$N$_2$O$_4$S requires 349.1222).

Compound 2

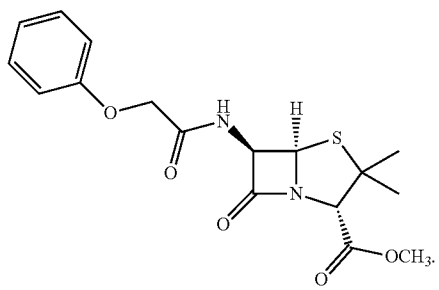

2

Methyl(2S,5R,6R)-3,3-dimethyl-7-oxo-6-(2-phenoxyacetamido)-4-thia-1-azabicyclo[3.2.0]heptane-2-carboxylate (2). A total of 346 mg (95%) methyl ester 2 was obtained as a colorless oil. $^1$H NMR (400 MHz, CDCl$_3$) δ 7.33 (d, J=9.2 Hz, 1H), 7.28-7.23 (m, 1H), 6.97 (t, J=7.4 Hz, 1H), 6.87 (d, J=7.8 Hz, 1H), 5.68 (d, J=4.3, 1H), 5.53 (d, J=4.3, 1H), 4.49 (s, 2H), 4.41 (s, 1H), 3.71 (s, 3H), 1.54 (s, 3H), 1.43 (s, 3H); $^{13}$C NMR (101 MHz, CDCl$_3$) δ 173.0, 168.0, 156.9, 130.0, 129.6, 129.5, 122.1, 114.8, 114.6, 70.5, 67.7, 67.1, 64.7, 58.1, 52.5, 31.9, 26.9; IR (film) ν$_{max}$ 3333, 2924, 2854, 1779, 1736, 1686, 1659, 1497, 1211, 910, 725 cm$^{-1}$; HRMS (ESI) m/z 365.1176 (M+H$^+$, C$_{17}$H$_{21}$N$_2$O$_5$S requires 365.1171).

Compound 3

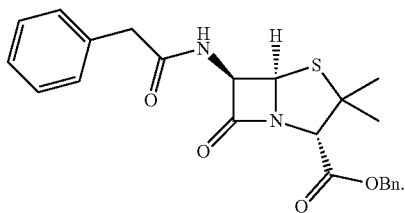

3

Benzyl(2S,5R,6R)-3,3-dimethyl-7-oxo-6-(2-phenylacetamido)-4-thia-1-azabicyclo[3.2.0]heptane-2-carboxylate (3). A total of 204 mg (48%) benzyl ester 3 was obtained as a yellow viscous oil. $^1$H NMR (400 MHz, CDCl$_3$) δ 7.50-7.05 (m, 10H), 6.34 (d, J=8.4 Hz, 1H), 5.56 (d, J=4.1 Hz, 1H), 5.39 (dd, J=8.4, 4.1 Hz, 1H), 5.07 (s, 2H), 4.32 (s, 1H), 3.51 (s, 2H), 1.32 (s, 3H), 1.27 (s, 3H); $^{13}$C NMR (101 MHz, CDCl$_3$) δ 173.4, 170.5, 168.0, 134.8, 133.9, 129.7, 128.9, 128.8, 128.4, 127.3, 122.1, 115.46, 114.0, 70.4, 68.0, 64.8, 64.4, 58.9, 43.2, 31.9, 26.9; IR (film) ν$_{max}$ 3302, 2932, 1780, 1736, 1651, 1497, 1296, 1188, 910, 725 cm$^{-1}$; HRMS (ESI) m/z 425.1534 (M+H$^+$, C$_{23}$H$_{25}$N$_2$O$_4$S requires 425.1535).

Compound 4

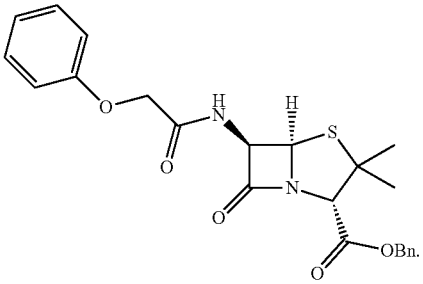

4

Benzyl(2S,5R,6R)-3,3-dimethyl-7-oxo-6-(2-phenoxyacetamido)-4-thia-1-azabicyclo[3.2.0]heptane-2-carboxylate (4). A total of 247 mg (56%) benzyl ester 4 was obtained as a yellow viscous oil. $^1$H NMR (400 MHz, CDCl$_3$) δ 7.38 (d, J=9.1 Hz, 1H), 7.32 (s, 5H), 7.25 (t, J=8.0 Hz, 2H), 6.97 (t, J=7.4 Hz, 1H), 6.87 (d, J=8.0 Hz, 2H), 5.66 (dd, J=9.1, 4.2 Hz, 1H), 5.52 (d, J=4.2 Hz, 1H), 5.13 (s, 2H), 4.47 (s, 2H), 1.51 (s, 3H), 1.37 (s, 3H); $^{13}$C NMR (101 MHz, CDCl$_3$) δ 172.9, 167.9, 156.9, 134.7, 130.0, 129.5, 128.9, 128.4, 128.1, 122.4, 122.1, 115.4, 114.8, 114.6, 114.0, 70.3, 67.9, 67.5, 64.8, 58.3, 58.1, 32.2, 26.8; IR (film) ν$_{max}$ 3294, 3032, 2963, 2870, 1789, 1744, 1651, 1512, 1273, 1211, 1188, 717 cm$^{-1}$; HRMS (ESI) m/z 441.1484 (M+H$^+$, C$_{23}$H$_{25}$N$_2$O$_5$S requires 441.1484).

Compound 5

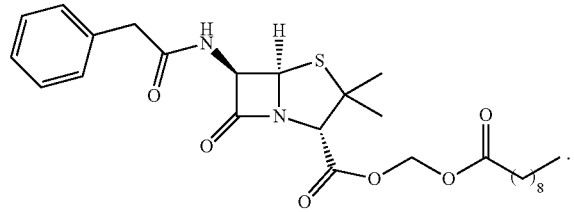

5

(Decanoyloxy)methyl (2S,5R,6R)-3,3-dimethyl-7-oxo-6-(2-phenylacetamido)-4-thia-1-azabicyclo[3.2.0]heptane-2-carboxylate (5). A total of 446 mg (86%) ester 5 was obtained as a colorless viscous oil. $^1$H NMR (400 MHz, CDCl$_3$) δ 7.40-7.07 (m, 5H), 6.43 (d, J=8.8 Hz, 1H), 5.74 (d, J=5.6 Hz, 1H), 5.68 (d, J=5.6 Hz, 1H), 5.56 (dd, J=8.8, 4.2 Hz, 1H), 5.42 (d, J=4.2 Hz, 1H), 4.32 (s, 1H), 3.55 (s, 2H), 2.27 (t, J=7.5 Hz, 2H), 1.54 (p, J=7.1 Hz, 2H), 1.38 (s, 6H), 1.40-1.10 (m, 14H), 0.81 (t, J=6.6 Hz, 3H); $^{13}$C NMR (101 MHz, CDCl$_3$) δ 173.4, 172.0, 170.6, 166.3, 134.0, 129.7, 129.2, 128.7, 127.7, 127.2, 79.5, 69.74, 68.0, 64.4, 59.0, 43.1, 33.7, 31.8, 31.5, 29.3, 29.1, 28.9, 26.7, 24.4, 22.6, 14.1, 14.0; IR (film) ν$_{max}$ 3309, 2924, 2855, 1759, 1658, 1519, 1103, 725 cm$^{-1}$; HRMS (ESI) m/z 541.2337 (M+Na$^+$, C$_{27}$H$_{38}$N$_2$O$_6$SNa requires 541.2348).

Compound 6

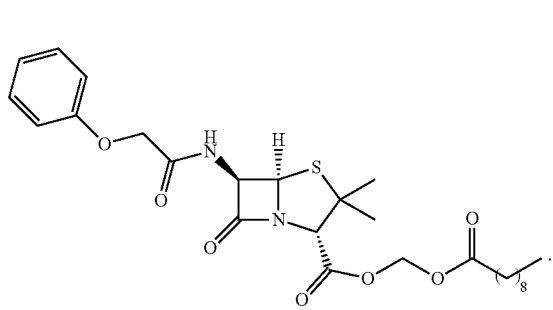

(Decanoyloxy)methyl(2S,5R,6R)-3,3-dimethyl-7-oxo-6-(2-phenoxyacetamido)-4-thia-1-azabicyclo[3.2.0]heptane-2-carboxylate (6). A total of 352 mg (81%) ester 5 was obtained as a colorless viscous oil. $^1$H NMR (400 MHz, CDCl$_3$) δ 7.33 (d, J=9.2 Hz, 1H), 7.26 (t, J=9.2 Hz, 2H), 6.98 (t, J=7.4 Hz, 1H), 6.87 (d, J=7.9 Hz, 2H), 5.79 (d, J=5.6 Hz, 1H), 5.72 (d, J=5.6 Hz, 1H), 5.69 (dd, J=9.2, 4.3 Hz, 1H), 5.53 (d, J=4.3 Hz, 1H), 4.51 (s, 2H), 4.43 (s, 1H), 2.31 (t, J=7.5 Hz, 2H), 1.62-1.55 (m, 2H), 1.54 (s, 3H), 1.45 (s, 3H), 1.30-1.15 (m, 12H), 0.83 (t, J=7.6 Hz, 1H); $^{13}$C NMR (101 MHz, CDCl$_3$) δ 173.0, 172.1, 168.0, 166.4, 156.9, 130.0, 129.5, 122.2, 114.8, 114.6, 79.5, 70.0, 67.8, 67.0, 64.7, 58.0, 33.7, 31.8, 29.3, 29.2, 28.9, 26.8, 26.5, 24.5, 22.6, 14.1, 14.0; IR (film) $v_{max}$ 3341, 2924, 2854, 1759, 1681, 1500, 980, 723 cm$^{-1}$; HRMS (ESI) m/z 535.2469 (M+H$^+$, C$_{27}$H$_{39}$N$_2$O$_7$S requires 535.2478).

Compound 8

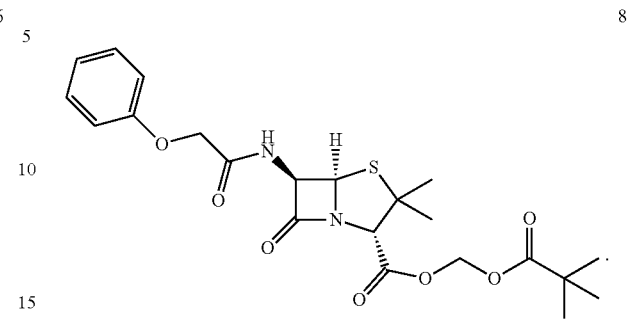

(Pivaloyloxy)methyl (2S,5R,6R)-3,3-dimethyl-7-oxo-6-(2-phenoxyacetamido)-4-thia-1-azabicyclo[3.2.0]heptane-2-carboxylate (8). A total of 381 mg (82%) ester 8 was obtained as a pale yellow viscous oil. $^1$H NMR (400 MHz, CDCl$_3$) δ 7.34 (d, J=9.1 Hz, 1H), 7.30-7.21 (m, 2H), 7.01-6.93 (m, 1H), 6.88 (dt, J=13.1, 9.3 Hz, 2H), 5.82 (d, J=5.5 Hz, 1H), 5.73 (d, J=5.5 Hz, 1H), 5.69 (dd, J=9.2, 4.3 Hz, 1H), 5.53 (d, J=4.3 Hz, 1H), 4.52 (s, 2H), 4.44 (s, 1H), 1.54 (s, 3H), 1.47 (s, 3H), 1.17 (s, 9H); $^{13}$C NMR (101 MHz, CDCl$_3$) δ 176.8, 172.9, 168.1, 166.3, 156.8, 130.0, 129.5, 122.2, 114.8, 114.6, 79.8, 70.0, 67.7, 67.0, 64.7, 58.0, 38.7, 31.8, 26.7; IR (film) $v_{max}$ 3302, 2970, 2932, 2877, 1751, 1658, 1520, 1103, 980 cm$^{-1}$; HRMS (ESI) m/z 465.1696 (M+H$^+$, C$_{22}$H$_{29}$N$_2$O$_7$S requires 465.1695).

Compound 7

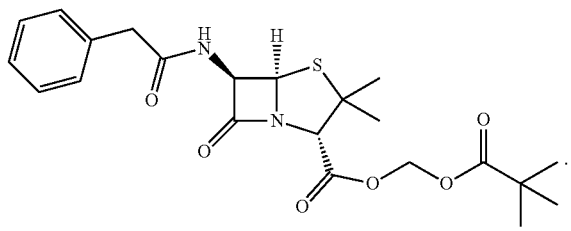

(Pivaloyloxy)methyl (2S,5R,6R)-3,3-dimethyl-7-oxo-6-(2-phenylacetamido)-4-thia-1-azabicyclo[3.2.0]heptane-2-carboxylate (7). A total of 367 mg (82%) ester 7 was obtained as a pale yellow viscous oil viscous oil. $^1$H NMR (400 MHz, CDCl$_3$) δ 7.35-7.10 (m, 5H), 6.82 (d, J=8.2 Hz, 1H), 5.88-5.54 (m, 3H), 5.45 (t, J=4.0 Hz, 1H), 4.35 (s, 1H), 3.54 (s, 2H), 1.41 (s, 6H), 1.15 (s, 9H); $^{13}$C NMR (101 MHz, CDCl$_3$) δ 176.8, 173.4, 170.4, 166.3, 133.9, 129.7, 129.3, 128.8, 127.8, 127.3, 79.8, 69.8, 68.0, 64.4, 58.9, 50.5, 43.2, 38.7, 31.8, 26.7; IR (film) $v_{max}$ 3333, 2970, 2877, 1751, 1674, 1490, 1103, 980 cm$^{-1}$; HRMS (ESI) m/z 471.1571 (M+Na$^+$, C$_{22}$H$_{28}$N$_2$O$_6$SNa requires 471.1566).

Compound 9

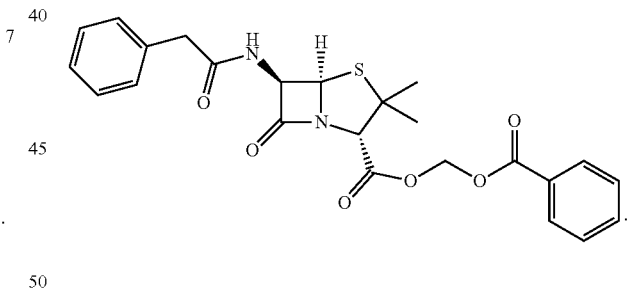

(Pivaloyloxy)methyl (2S,5R,6R)-3,3-dimethyl-7-oxo-6-(2-phenylacetamido)-4-thia-1-azabicyclo[3.2.0]heptane-2-carboxylate (9). A total of 304 mg (65%) ester 9 was obtained as a brown viscous oil which decomposes upon standing. $^1$H NMR (400 MHz, CDCl$_3$) δ 8.10 (d, J=6.1 Hz, 2H), 7.51 (t, J=8.2 Hz, 1H), 7.50-7.05 (m, 7H), 6.81 (d, J=8.2 Hz, 1H), 5.88-5.54 (m, 3H), 5.45 (t, J=4.0 Hz, 1H), 4.35 (s, 1H), 3.52 (s, 2H), 1.39 (s, 6H); $^{13}$C NMR (101 MHz, CDCl$_3$) δ 176.9, 172.9, 170.3, 166.0, 133.7, 133.3, 129.8, 129.77, 129.71, 129.3, 128.8, 128.4, 127.8, 127.3, 79.9, 69.8, 68.00, 64.4, 58.9, 50.5, 31.6, 26.8; IR (film) $v_{max}$ 3240, 2924, 2854, 1718, 1674, 1490, 1103, 1025, 980, 915 cm$^{-1}$; HRMS (ESI) m/z 491.1244 (M+Na$^+$, C$_{24}$H$_{24}$N$_2$O$_6$SNa requires 491.1253).

Compound 10

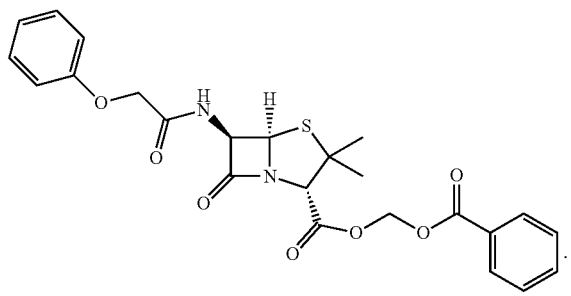

(Benzoyloxy)methyl (2S,5R,6R)-3,3-dimethyl-7-oxo-6-(2-phenoxyacetamido)-4-thia-1-azabicyclo[3.2.0]heptane-2-carboxylate (10). A total of 368 mg (76%) ester 10 was obtained as a brown viscous oil which decomposes upon standing. $^1H$ NMR (400 MHz, $CDCl_3$) δ 8.09 (d, J=6.4 Hz, 2H), 7.57 (t, J=8.2 Hz, 1H), 7.44 (dd, J=6.4, 8.2 Hz, 2H), 7.36-7.21 (m, 3H), 7.05-6.95 (m, 1H), 6.87 (dt, J=13.0, 9.2 Hz, 2H), 5.83 (d, J=5.5 Hz, 1H), 5.73 (d, J=5.5 Hz, 1H), 5.65 (dd, J=9.2, 4.2 Hz, 1H), 5.51 (d, J=4.2 Hz, 1H), 4.52 (s, 2H), 4.43 (s, 1H), 1.55 (s, 3H), 1.47 (s, 3H); $^{13}C$ NMR (101 MHz, $CDCl_3$) δ 176.7, 173.0, 168.1, 166.0, 156.8, 133.2, 130.1, 129.79, 129.72, 129.5, 128.3, 122.3, 114.7, 114.5, 80.1, 70.0, 67.8, 67.1, 64.6, 57.9, 31.5, 26.8; IR (film) $v_{max}$ 3320, 2931, 2856, 1717, 1674, 1490, 1095, 1024, 978, 914 $cm^{-1}$; HRMS (ESI) m/z 507.1201 ($M+Na^+$, $C_{24}H_{24}N_2O_7SNa$ requires 507.1202).

Each of the synthesized penicillin derivatives, product compounds 1-10, was applied in a 1:1 mixture with horticultural oil, a dosage of 25 μmoles of each product compound was applied to the leaves and stems of approximately 0.5 g of Murcott mandarin clippings. The horticultural oil used was neem oil. Neem oil is a vegetable oil pressed from the fruits and seeds of the neem tree, *Azadirachta indica*, an evergreen tree endemic to the Indian subcontinent. The compounds 1-10 can be dissolved in the neem oil, compounds 1 and 2 formed more of an emulsion than a solution. Once mixed with the neem oil the solutions can be mixed with water and spray applied. The clippings, which consisted of two leaves and an internode, were coated evenly with the product compound while leaving a void region on the bottom to midsection of the internode region to avoid a false positive in the analysis. Once coated, the bottom portion of the internode, which was not coated with any penicillin ester, was submerged in a 1 mL reservoir of tap water and the clipping was allowed to incubate for a 24 hour period. After 24 hours the reservoir water was diluted with 1 mL of methanol, filtered through a nylon 0.2 μm microfilter, and analyzed by native mode ESI mass spectrum analysis at an injection rate of 10 mL/min. Untreated clippings and clippings treated only with horticultural oil were used as controls. Through this method of detection, peaks in the mass spectrum were identified that correspond to masses of penicillin G or penicillin V as well as to documented penicillin metabolites for both antibiotics.

EXPERIMENTAL RESULTS

Figure 12:
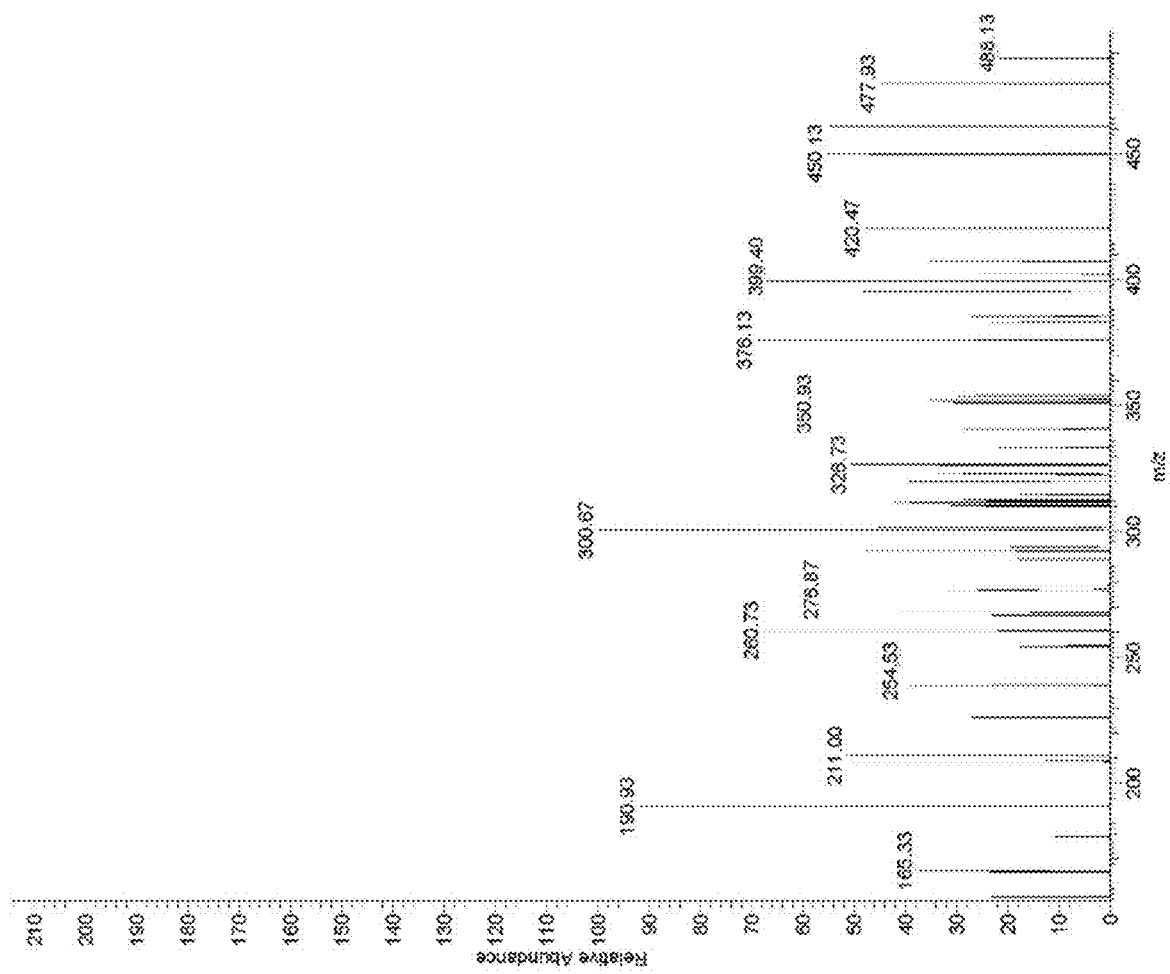
Figure 13:
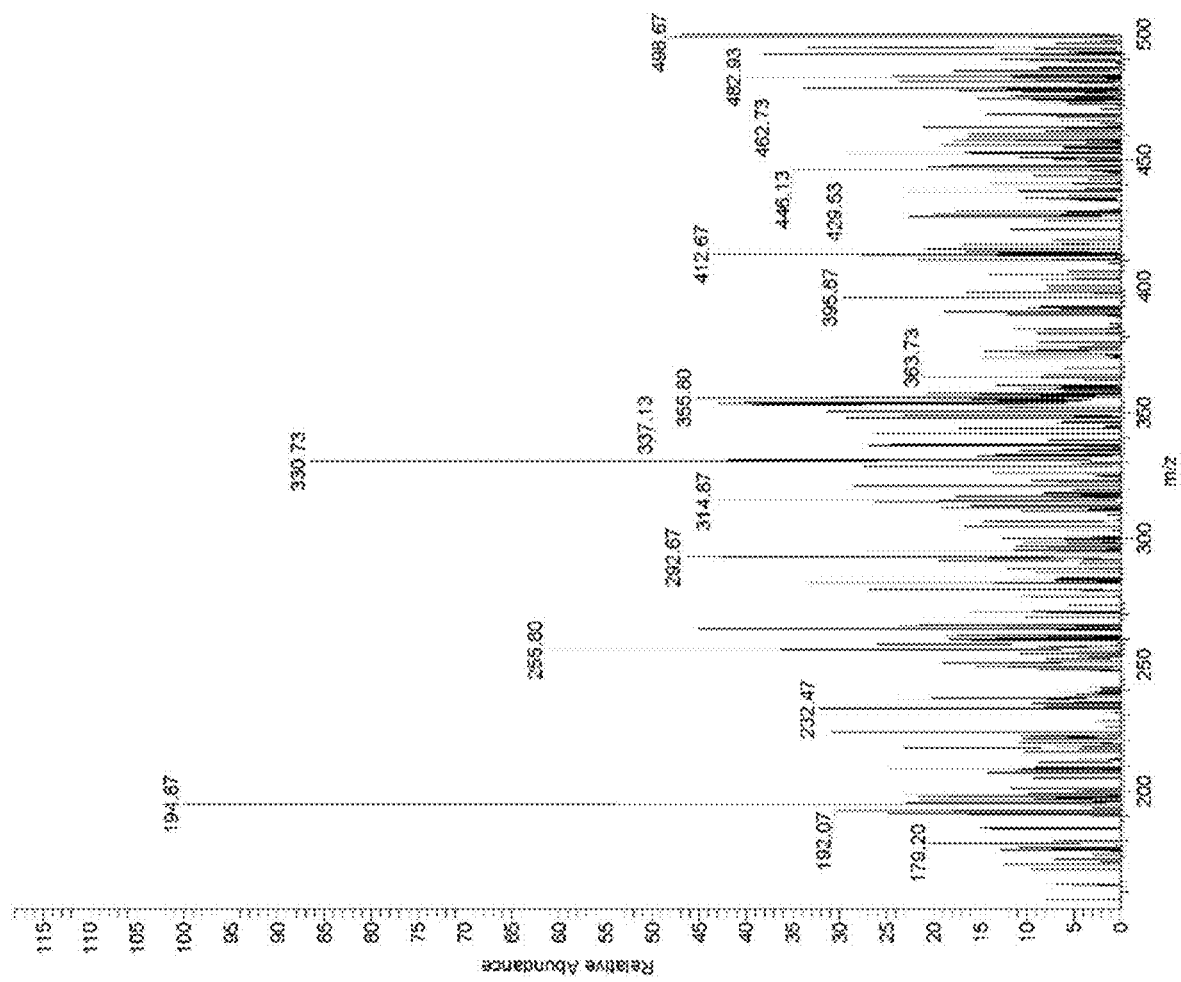
Figure 14:
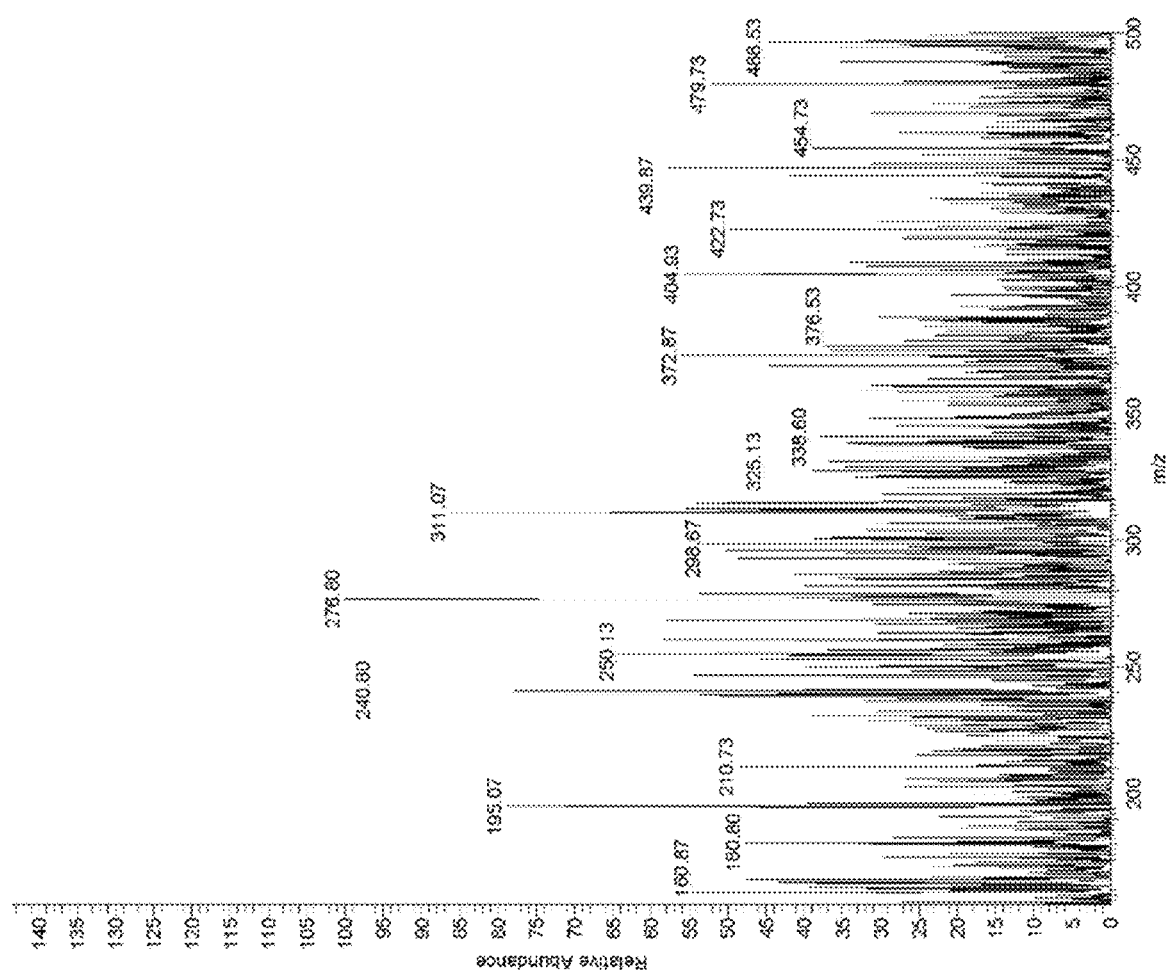
Figure 15:
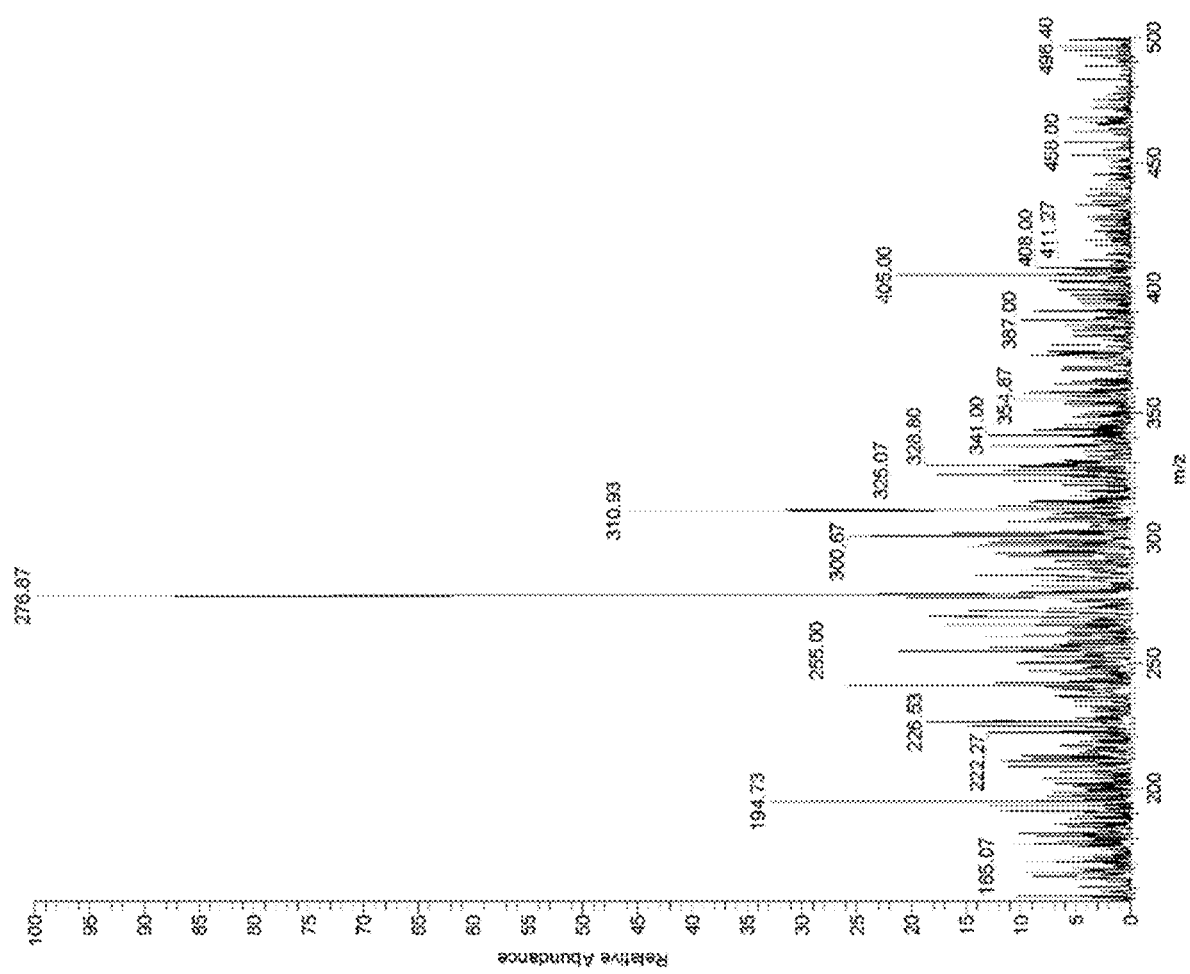
Figure 16:
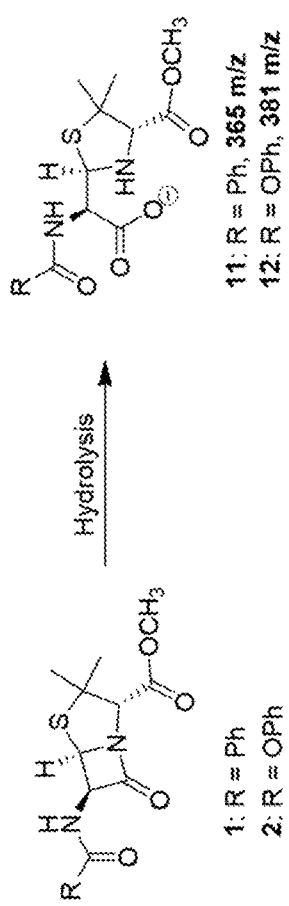

The general reaction scheme detailed above was used to create the 10 ester derivatives of penicillin G or penicillin V shown in FIG. 2B to 2F. The measured log $K_{ow}$ for each product compound is shown in FIG. 2B to 2F. The product compounds 1-10 were designed to exhibit a range of log $K_{ow}$ values between 0.7 to 5.0. Two of the product compounds, 5 and 6, had log $K_{ow}$ values close to that of the PRIOR ART Spinosyn A, which is an insecticide that is known to readily penetrate citrus leaves.

The synthesis components and yields for the ten product compounds are shown in Table 2 below. Most of the yields for the $S_N2$ reaction were moderate to good, ranging from 65-86%, with the exception of $(C_6H_5)CH_2Br$ which gave relatively low yields of 48% and 56% of the benzyl esters of penicillin G and penicillin V respectively. Methyl esters, product compounds 1 and 2, both were formed with exceptional yields of 92% for penicillin G and 95% for penicillin V.

TABLE 2

| Penicillin | Alkyl or Aryl halide | Product compound | % yield after purification |
|---|---|---|---|
| G | $CH_3I$ | 1 | 92 |
| G | $(C_6H_5)CH_2Br$ | 3 | 48 |
| G | $ClCH_2O_2C(CH_2)_8CH_3$ | 5 | 86 |
| G | $ClCH_2CO_2C(CH_3)_3$ | 7 | 82 |
| G | $ClCH_2OCO(C_6H_5)$ | 9 | 65 |
| V | $CH_3I$ | 2 | 95 |
| V | $(C_6H_5)CH_2Br$ | 4 | 56 |
| V | $ClCH_2O_2C(CH_2)_8CH_3$ | 6 | 81 |
| V | $ClCH_2CO_2C(CH_3)_3$ | 8 | 82 |
| V | $ClCH_2OCO(C_6H_5)$ | 10 | 76 |

The negative ESI mass spectrum of the reservoir water for clippings treated with the product compounds 1-10 and the controls are shown in FIG. 4-15. The ESI show a number of surprising results. When the reservoirs of water for clippings treated with product compounds 1 or 2, the methyl esters, were analyzed by negative ESI mass spectrum base peaks of 364.73 m/z, metabolite 11, and 380.73 m/z, metabolite 12, were detected as shown in FIG. 4 and FIG. 5. These peaks likely correspond to metabolites of product compounds 1 and 2, in which the beta-lactam ring has been hydrolyzed but the methyl ester group has remained intact, see FIG. 16 for a proposed scheme. Metabolites 11 and 12 would suggest that product compounds 1 and 2 can successfully diffuse through the waxy cuticle layer and into the phloem of the citrus clippings, however, they are not being successfully metabolized to the active antibiotic. Instead, the beta-lactam ring appears to be hydrolyzing at a faster rate than the methyl ester group, perhaps due to reduced accessibility of methyl esterases to the methyl ester group via steric hindrance. Substituting the methyl ester group with a benzyl ester, a form of an aryl halide, as in product compounds 3 and 4 appears to substantially reduce permeability, as no recognizable metabolite peaks were detected for these product compounds, see FIG. 6 and FIG. 7.

The decanoyloxymethyl, product compounds 5 and 6, and the pivaloyloxymethyl esters, product compounds 7 and 8, displayed the most promising results in which the base peaks in the mass spectrum corresponded to the active antibiotics penicillin G at approximately 333 m/z (332.60 to 332.67) or penicillin V at approximately 349 m/z (348.67 to 348.87) and/or known metabolites with an identical molecular weight. See the results shown in FIG. 8-FIG. 11. The presence of the penicillin G or V would suggest that these penicillin esters derived from oxymethyl alkyl halides are successfully penetrating the waxy cuticle layer, the epidermis, and diffusing into the phloem. Along the way they are being hydrolyzed into the active beta-lactam antibiotic. It is unapparent, however, whether the decanoyloxymethyl and pivaloyloxymethyl ester groups are being hydrolyzed enzymatically or through a spontaneous hydrolysis process to produce the active penicillin, though the latter is more common in mammalian systems. Surprisingly, the benzoyloxymethyl product compounds, 9 and 10, did not result in detectable 333 m/z or 349 m/z or recognizable metabolite peaks in the mass spectrum. See FIG. 12 and FIG. 13 for the results of using these oxymethyl aryl halides. In considering the structural similarities of product compounds 9 and 10 with product compounds 3 and 4, it may be possible that a benzyl group proximal to the penicillin ester either deters the diffusion into phloem or prevents hydrolysis of the ester group within the plant. The results shown in FIGS. 14 and 15 show that these identified peaks are not seen in the control reservoir water samples.

A small library of ten penicillin G and V esters were evaluated for their ability to penetrate the waxy cuticle layer and to be converted into active antibiotics by citrus tissue. Product compounds 1, 2, 5, 6, 7, and 8 all appear to affectively penetrate through the waxy cuticle layer and through the epidermis to access the phloem within Murcott mandarin clippings. However, only product compounds 5, 6, 7, and 8 appeared to be hydrolyzed into the active antibiotic. The results suggest that product compounds 5, 6, 7, and 8 could be used as a method for delivering beta-lactam antibiotics into the phloem of citrus plants infected with *Candidatus liberbacter*, and therefore could serve as a means of treating HLB disease. This delivery mechanism is far more effective, practical, economical, and considerate of environmental antibiotic resistance compared to the current methods being applied, especially when considering that in our system active antibiotics are only produced by esterase activity that occurs within the citrus plant. It is believed that the masking process of the present disclosure will enable modification of a variety of beta-lactam antibiotics and open up their use to combat plant bacterial infections that currently cannot be controlled. The ester masked beta-lactam can be applied to the outside surface of a plant with a bacterial infection to control or prevent the infection. The amount of ester masked beta-lactam applied to a plant will be determined in part by the activity of the beta-lactam against the particular infection, the degree of infection and other factors known to one of skill in the art. Exemplary classes of beta-lactam antibiotics that could be used in the present disclosure and method include: penams, carbapenams, oxapenams, monobactams, cephems, carbacephems, oxacephems and mixtures thereof. Suitable penams and carbapenams include, by way of example only and not limitation, benathine penicillin, benzylpenicillin (penicillin G), phenoxymethylpenicillin (penicillin V), procaine penicillin, cloxacillin, dicloxacillin, flucloxacillin, methicillin, nafcillin, oxacillin, temocillin, amoxicillin, ampicillin, mecillinam, carenicillin, ticarcillin, azlocillin, mezlocillin, piperacillin, biapenem, doripenem, ertapenem, faropenem, imipenem, meropenem, panipenem, razupenem, tebipenem, and thienamycin. Suitable cephems and carbacephems include, by way of example only and not limitation, cefazolin, cephalexin, cephalosporin C, cephalothin, cefaclor, cefamandole, cefuroximine, cefotetan, cefoxitin, cefixime, cefotaxime, cefpodoxime, ceftazidime, ceftriaxone, cefepime, cefpirome, and ceftaroline. Suitable monobactams include, by way of example only and not limitation, aztreonam, tigemonam, nocardicin A, and tabtoxinine β-lactam.

FIG. 16 shows the proposed hydrolysis of the beta-lactam ring for product compounds 1 and 2, the methyl esters of Penicillin G and V, which is believed to occur based on the ESI results.

The foregoing disclosure has been described in accordance with the relevant legal standards, thus the description is exemplary rather than limiting in nature. Variations and modifications to the disclosed embodiment may become apparent to those skilled in the art and do come within the scope of the disclosure. Accordingly, the scope of legal protection afforded this disclosure can only be determined by studying the following claims.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

I claim:

1. A method of treating a bacterial infection, wherein the bacterial infection is Huanglongbing in a citrus plant comprising the steps of:

a) identifying a citrus plant having a bacterial infection of Huanglongbing;

b) providing a methylene ester alkyl modified beta-lactam antibiotic, wherein the methylene ester alkyl modified beta-lactam antibiotic is obtained by reacting the carboxylate functionality of a beta lactam antibiotic selected from the group consisting of benzyl penicillin, phenoxymethylpenicillin, and mixtures thereof with an oxymethyl alkyl halide to form a beta-lactam antibiotic having two ester groups separated by a methylene group and with an alkyl group pending from one of said two ester groups; and c) applying a composition consisting of the methylene ester alkyl modified beta-lactam antibiotic of step b) and a carrier vehicle to an outside surface of the plant having the bacterial infection in an amount sufficient to treat the bacterial infection, wherein the carrier vehicle is selected from the group consisting of a horticultural oil, water, or a combination thereof.

2. The method according to claim 1, wherein in step b), the oxymethyl alkyl halide is selected from the group consisting of a decanoyl oxymethyl alkyl halide, a pivaloyl oxymethyl halide or a mixture thereof in an organic solvent.

3. The method according to claim 2, wherein step b) comprises reacting the beta-lactam antibiotic with the oxymethyl alkyl halide in a molar ratio of 1:10.

4. The method according to claim 2, wherein the organic solvent comprises N,N dimethylforamide.

5. The method according to claim 2, wherein step b) comprises reacting the reaction mixture at a temperature of at least 25° C. for at least 1 hour.

6. The method according to claim 2, where in step b) the reaction is quenched by addition of water and the methylene ester alkyl modified beta-lactam antibiotic product compound is extracted from the reaction mixture into an organic solvent.

7. The method according to claim 6, wherein the extracted product compound is further passed through a flash column chromatography purification process.

8. The method of claim 1, wherein the carrier vehicle is a horticultural oil.

9. The method of claim 8, wherein the horticultural oil is neem oil.

10. The method of claim 1, wherein the carrier vehicle is water.

11. The method according to claim 1, wherein step c) is a foliar application.

12. The method according to claim 1, wherein the carrier vehicle is a mixture of the horticultural oil and water.

13. The method according to claim 2, wherein the oxymethyl alkyl halide is a decanoyl oxymethyl halide.

* * * * *